United States Patent [19]
Berk et al.

[11] Patent Number: 6,159,009
[45] Date of Patent: Dec. 12, 2000

[54] DENTAL AMALGAM CARRIER WITH REPLACEABLE SLEEVES AND CARTRIDGES

[75] Inventors: Kenneth J. Berk, Newton; Fredrick M. Berk, Brookline; Donald Berk, Newton, all of Mass.; Russell D. Jenkins, Ronan, Mont.

[73] Assignee: Pulpdent Corporation, Watertown, Mass.

[21] Appl. No.: 09/325,126

[22] Filed: Jun. 7, 1999

[51] Int. Cl.[7] .................................................. A61C 3/08
[52] U.S. Cl. ............................................. 433/164; 433/90
[58] Field of Search ................... 433/164, 90, 89

[56] References Cited

U.S. PATENT DOCUMENTS

| 4,273,534 | 6/1981 | Seid | 433/90 |
| 4,515,563 | 5/1985 | Dungill | 433/90 |
| 5,580,245 | 12/1996 | Nevin | 433/90 |

*Primary Examiner*—John J. Wilson
*Assistant Examiner*—Melba Bumgarner
*Attorney, Agent, or Firm*—Lee & Hollander

[57] ABSTRACT

An improved amalgam or resin carrier, which has a plunger and lever mechanism similar to the well-known lever-actuated carrier and which has an easily replaceable sleeve or barrel for holding highly filled materials. The barrel may be easily removed for maintenance, cleaning, or replacement. In an alternate configuration, the barrel may be preloaded with a packable composite dental resin, thus allowing quick and easy clinical use. The preloaded barrel may be manufactured in the form of a disposable cartridge, and is especially suitable for use with light-activated materials.

16 Claims, 2 Drawing Sheets

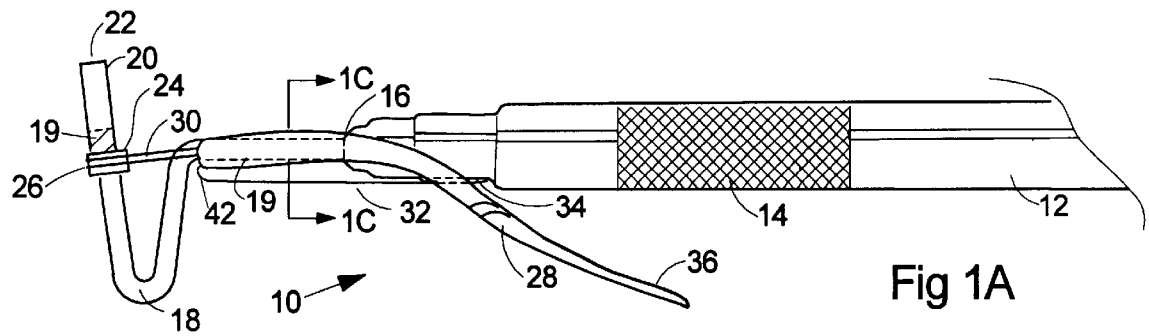
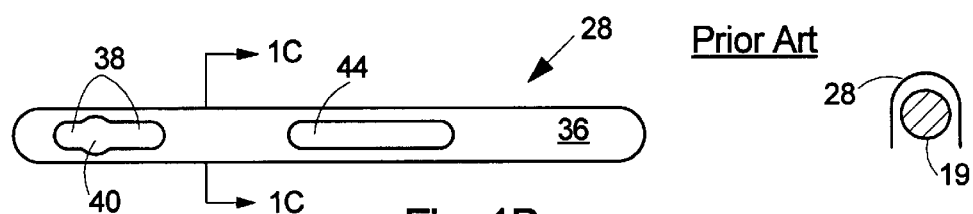
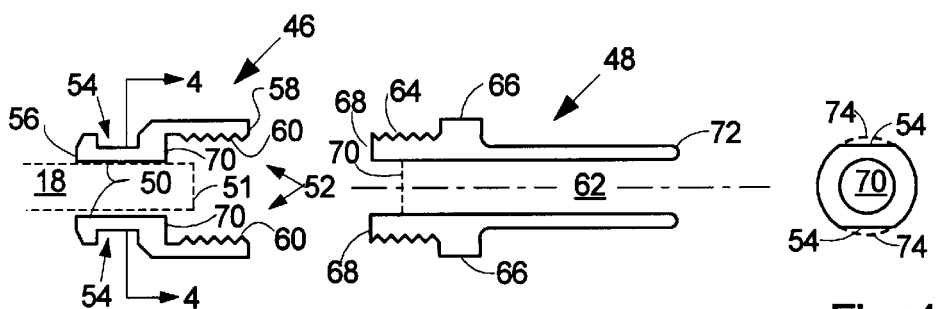
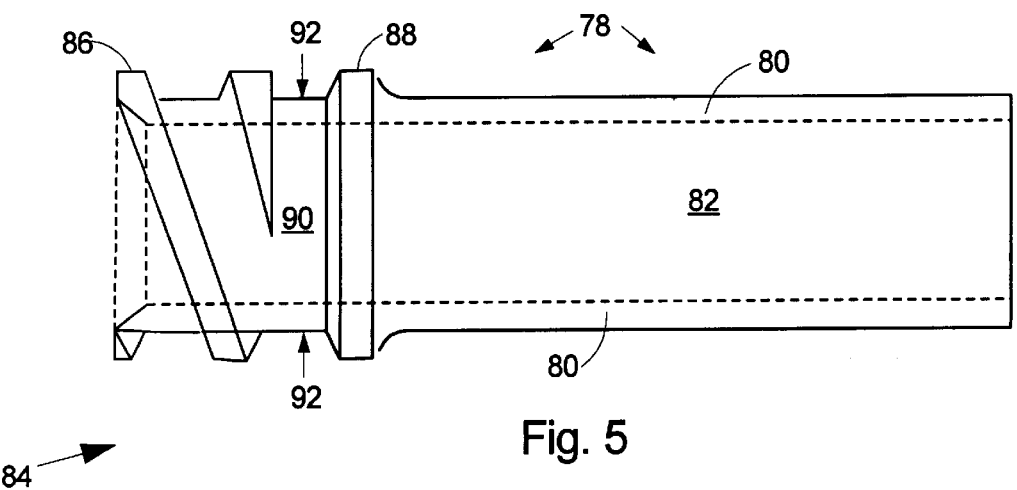

DENTAL AMALGAM CARRIER WITH REPLACEABLE SLEEVES AND CARTRIDGES

FIELD OF THE INVENTION

The present invention relates to dental instruments and more particularly devices for applying dental materials to a patient's teeth

BACKGROUND OF THE INVENTION

Conventional lever-activated amalgam carriers are well known and popular devices for filling dental cavities with amalgam or other materials. These devices typically include a hollow cylinder or sleeve into which the filling material is loaded, a plunger that is used to push out the material, and a lever which controls the movement of the plunger in the sleeve. U.S. Pat. No. 1,797,866 of C. S. Ivory is an early example of such an amalgam carrier. The construction and operation of amalgam carriers are well-known, and various modification of the basic construction described above have been developed. See, for example, the above-cited Ivory patent and U.S. Pat. Nos. 4,306,863, 4,355,976, and 4,273,543, the contents of which are incorporated by reference.

One problem that has confronted the art is the deterioration of the movable sleeve with use. Especially when amalgam filling materials are used, the interior of the sleeve becomes scratched and pitted. This increases the chances for contamination and also interferes with the smooth operation of the device. With current designs, the entire instrument must be disassembled in order to replace the sleeve, which is a time-consuming and delicate task.

Recently, dentists have been increasingly using dental composite resins for fillings and other restorative procedures. These materials are malleable when first dispensed for their intended use. One popular type of dental composite hardens by exposing the material to light, typically of a particular wavelength and intensity, to initiate polymerization. Other composite materials harden when the mixing of multiple components initiates polymerization.

A popular device among dentists for applying these materials is the system made popular by Dr. William Dragon and Centrix, Inc. An example of this is shown in U.S. Pat. No. 4,619,613. In this system, dental composite materials are loaded into cartridges by dental office personnel, or they may be preloaded into cartridges by dental manufacturers. These cartridges are then loaded into a syringe or gun-type apparatus for extruding the material into the oral cavity. This system is best used with materials having adequate flow characteristics to allow the extrusion of the composite material.

Recently, so-called "packable" composite dental filling materials have been developed. These materials are very hard and dense, and they have poor flow characteristics in the unpolymerized state. These packable composites are physically approaching the feel, handling, and packability of traditional dental amalgams, and as a result, lever-type amalgam carriers have become popular instruments for handling and conveying these composite resin materials. The present invention addresses the specific requirements of these packable composite materials and the need for a carrier designed to accommodate the special packaging and clinical handling of packable dental composite resins.

SUMMARY OF THE INVENTION

The present invention includes a new type of resin carrier, which has a plunger and lever mechanism similar to the well-known lever-actuated carrier and which has an easily replaceable sleeve or barrel for holding highly filled materials. The barrel may be easily removed for maintenance, cleaning, or replacement. In an alternate configuration, the barrel may be preloaded with a packable composite dental resin, thus allowing quick and easy clinical use. The preloaded barrel may be manufactured in the form of a disposable cartridge so that it would be disposed of and replaced after use, rather than requiring refilling when spent.

The removable barrel may be made of various materials, including stainless or other metals and plastic materials. Preloaded disposable cartridges containing light-activated materials may be easily made of materials that are opaque or which block light of the activating frequency.

DESCRIPTION OF THE DRAWINGS

The advantages and operation of the present invention are more fully set forth in the following description of the preferred embodiment and by reference to the drawings, of which:

FIGS. 1A, 1B, and 1C show the construction and of a typical prior art amalgam carrier having a tubular sleeve assembly held within the confines of a slot in the lever mechanism;

FIGS. 2, 3, and 4 show the details of the receiving body and barrel of the present invention; and FIG. 5 shows an alternate embodiment of the present invention which utilizes a barrel which attaches directly to the lever;

DESCRIPTION OF THE PREFERRED EMBODIMENT

Figure 6:
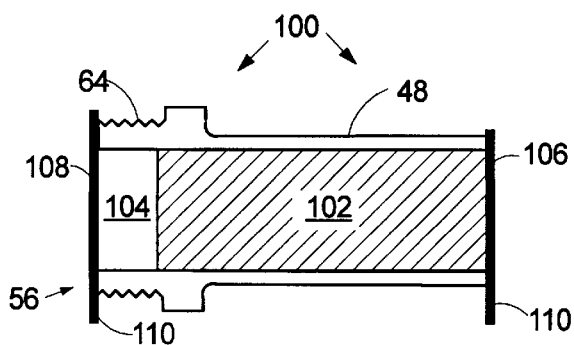
FIG. 6 shows a preloaded cartridge.

FIG. 1A shows an exemplary, lever-actuated amalgam carrier of the type known in the prior art, the description which will be helpful in understanding the present invention. The carrier includes an elongated handle portion 12 which is attached to a plunger 18 at the distal end 16 of the handle. The handle 12 is typically round or polygonal in cross section and may have knurling or other machining to aid in gripping the handle.

Plunger 18 is typically formed of a stainless rod. It extends from the handle forward through a u-shaped section of a lever mechanism 28, described below, as shown by dotted lines 19, and is formed into the hook shape shown in FIG. 1A having a straight section at its distal end. A hollow sleeve 20 is slidably disposed over the straight portion of plunger 18. In the non-actuated position shown in FIG. 1A, the plunger extends partway into the bore 22 of sleeve 20 leaving an open bore 22 within the sleeve which receives a filler material.

The lever 28 has an opening in the distal end which is engaged by a groove 26 formed in the proximal portion of the sleeve 20. Referring to FIG. 1B, which is a top view of lever 28, an oblong slot 38 is formed in the end of the lever. The distal end of slot 38 is sized so as to be captured by groove 26 in sleeve 20. A wider portion 40 of slot 38 allows the sleeve 20 to be inserted into the lever during assembly. Slot 38 is long enough to allow the hook portion of plunger 18 to extend through it, as shown in FIG. 1A.

Lever 28 is generally flat at its distal end and unshaped in its middle portion, as shown by the cross-section of FIG. 1C. An actuation portion 36 of the lever extends away from the handle 14, and is slightly curved at its actuation portion 36 to provide a comfortable feel. Lever 28 is typically formed of stainless sheet metal, bent to form the shape shown.

A spring 32 is disposed so as to apply upward pressure on the distal portion of the lever and is typically secured to the handle at a point 34 by means of a screw or other attachment means, not shown. Typically spring 32 has a hook 42 at its distal end which, in cooperation with the sleeve groove 26 disposed in slot 38, secures the lever in the longitudinal direction.

A second slot 44 begins at the portion of lever 28 where it bends away from the plunger portion 19 that it straddles, and the distal end of slot 44 provides a fulcrum for the lever. When pressure is applied to the actuation portion 36 of the lever, the distal end of the lever moves the sleeve 20 downwardly over the plunger 18 to expel the material within bore 22. The dimensions of the sleeve, lever, and plunger are chosen so that the distal end of plunger 18 slightly extends out of the end of sleeve 20 when the lever is fully actuated.

In the present invention, the sleeve 20 is replaced with a removable sleeve structure. A two-part sleeve is structure shown in FIGS. 2 and 3. The proximal portion of the two-part sleeve includes a receiving body 46 that is retained in the lever mechanism of the resin carrier. The distal portion of the two-part sleeve includes a barrel 48 which is removable and replaceable.

FIG. 2 is a lateral cross-sectional view of receiving body 46. It includes a proximal sliding section 50 and a distal receiving section 52. The inside of the sliding section 50 is cylindrical and is slightly greater than the diameter of plunger 18 so as to slidably engage the plunger. The inside diameter of section 50 is typically on the order of 0.080 to 0.130 inches, although other dimensions may be chosen. The distal receiving section 52 is cylindrical and larger in diameter than sliding section 50. The receiving section 52 includes threads 60 on its inside for retaining the barrel 48.

In order to facilitate the barrel being threaded into the receiving body 48, the receiving body includes a mechanism to prevent it from rotating in the slot 38 in lever 28. In the embodiment shown in FIG. 2, this is done by machining slots 54 into the sides of the sliding section that engages the lever slot 38. The circumferential groove 26 which engages the barrel in the lever of the amalgam carrier shown in FIG. 1 is replaced by parallel slots 54 on the outside of section 50 which engage the slot 38 in lever 36 to prevent rotation of the sliding section in the lever. FIG. 4 is a cross section of the sliding section taken at the location of the flats showing these flats 54 on either side of the proximal end of the distal end of the sliding section. In FIG. 4, the plunger slides within the opening 70, and dashed lines 74 represent the outer circumference of the distal end 56 of the sliding section 50.

The dimensions of the plunger and the receiving body are such that in the non-actuated position, the tip of the plunger extends slightly into the receiving section, as shown by dotted lines 51. The receiving body 46 is preferably made of stainless steel, although other materials may be used.

The barrel 48 is shown in FIG. 3 and is tubular in shape. It includes a hollow bore 62 of fixed diameter along its length substantially equal to the inside diameter of sliding section 50. At the proximal end of the barrel, the outside surface has threads 64 so that it may be threaded into corresponding threads 60 of the receiving body. A shoulder 66 located just distally of threads 64 is provided and serves as a stop by butting up against the distal end 58 of the receiving body 46 when the barrel is screwed into the receiving body. Alternatively, shoulder 66 may be omitted and the stop would be provided by the proximal end 68 of the barrel butting up against wall 70 of the receiving body. When the barrel is completely threaded into the receiving body, the tip of the plunger will extend a short distance into the proximal end of the barrel, as shown by line 70, when the lever is in the non-activated position. In the described embodiment, this distance is approximately 0.050 inches into the barrel.

FIG. 5 shows an alternate embodiment of the present invention which does not use a receiving body but rather has a unique sleeve that mates directly with an opening in the distal end of lever 28. In FIG. 5, the sleeve is shown and it has a circular, hollow bore 82 surrounded by cylindrical walls 80. At the proximal end 84 of the sleeve, is formed a short thread 86 which extends around the outside surface of the sleeve for approximately two turns. A circumferential shoulder 88 is formed distally of the termination of thread 86 to provide a slot or groove 90 between the thread 86 and shoulder.

The sleeve of FIG. 5 is used with an amalgam carrier of the type shown in FIG. 1 constructed without the sleeve section 20 and in which the shape of slot 38 is modified to accept thread 86 in the proximal end of the sleeve 78. The thread 86, slot 90, and shoulder 88 are dimensioned so that the sleeve 78 can be directly threaded into the slot 38 in the end of lever 28, avoiding the necessity of either a sleeve 20 or a structure similar to the receiving body 46 shown in FIG. 2.

In use, the proximal end 84 of the sleeve of FIG. 5 is placed over the end of plunger 18 and the sleeve is rotated so that the groove of thread 86 engages the sides of slot 38 to pull in and secure the sleeve within the lever slot. When fully threaded into the slot, the lever will lie in slot 90, as indicated by arrows 92. The engagement of the thread 86 with the slot 38 can be aided by bending the slotted end of the lever to put a slight lateral twist in the slotted portion so that one side of slot 38 is slightly offset with respect to the opposite side.

The barrel of FIG. 3 and sleeve of FIG. 5 may be made of stainless or other metal or they may be fabricated from a plastic material, such as nylon, delrin, polypropylene, or other similar plastic. They may be formed by machining, injection molding, or other processes. The design of the present invention is especially applicable to being used in a system where disposable cartridges are pre-filled with a light-activated or other filling material. When the sleeve is to be preloaded with a light-activated filler, the sleeve should be opaque to light or be tinted to block light of the activating wavelength.

In FIG. 6, a sleeve 100 of the type shown in FIG. 3 is preloaded with a material 102 to be used for making a filling or for another purpose. The material is inset from the proximal end 56 of the sleeve to maintain a space 104 for the insertion of plunger 18 when the pre-filled cartridge 100 is threaded into the receiving body 46. The material 102 may extend to the distal end of the cartridge 100. Alternatively, if cartridges having differing amounts of material 102 are desired, the material need not extend to the distal end.

After being filled the ends of the sleeve 100 are preferably sealed, such as by sonic welding circular plastic or foil protective covers over the proximal and distal ends of the cartridge, as shown by covers 106 and 108 in FIG. 6. When provided with pull tabs 110, such covers may be quickly and easily removed by a dentist, and sonic welding eliminates the possibility of the filling material being contaminated by an adhesive.

Figure 7:
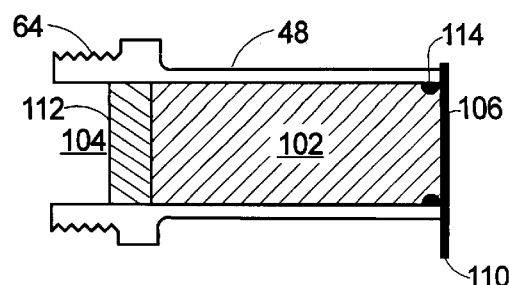
FIG. 7 shows a modified version of a preloaded cartridge which includes a disk at the proximal end of the preloaded material.

FIG. 7 shows an alternate embodiment for a pre-filled cartridge. In FIG. 7, a disk or plunger 112 has been added at the proximal end of the filler material 102. Disk 112 serves to retain the material 102 in place prior to use, and keeps the material from sagging into space 104 during shipment and handling. This embodiment is particularly useful with materials that are more fluid.

To provide a positive means of insuring that the disk 112 is not expelled from the distal end of the cartridge, a small ridge 114 can be added to the inside of the sleeve at its extreme distal end, as shown in FIG. 7. The ridge may be continuous around the end of the cylindrical bore or it may be discontinuous or it may consist of several small projections spaced around the distal end of the cartridge.

Figure 8B:
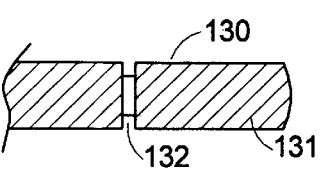
FIGS. 8A, 8B, and 8C show an alternate embodiment of the invention incorporating a cartridge with an integral plunger.
Figure 8A:
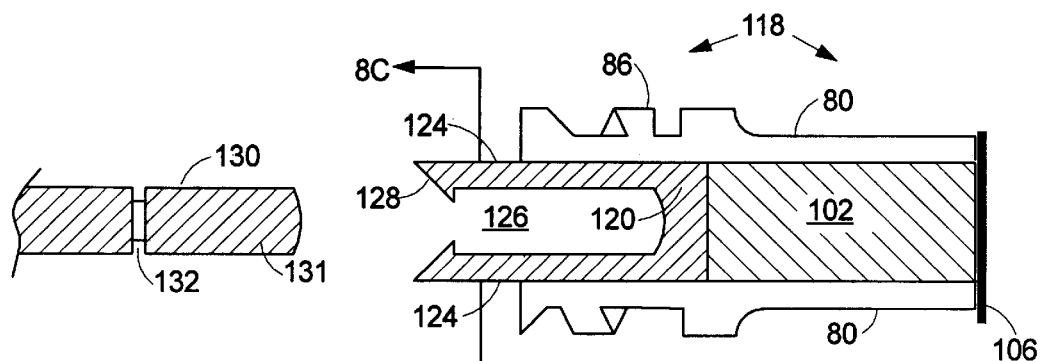
Figure 8C:
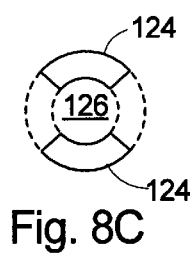

FIGS. 8A, 8B, and 8C show another embodiment of the invention particularly useful when prefilled with a material to provide a disposable cartridge. In FIG. 8A a sleeve of the type shown in FIG. 5 includes an integral plunger portion 120 located in the distal end of the cartridge 118 and abutting the preloaded material 102. Plunger 120 has two or more legs 124 extending rearwardly.

The cartridge of FIG. 8A works in conjunction with a plunger 130 having a modified distal end, as shown in FIG. 8B. Plunger 130 has its extreme distal tip shaped to fit inside the opening 124 between legs 126 of the cartridge plunger 120. A groove 132 is formed in the body of the plunger a short distance back from the tip. The groove engages hooks 128 formed in the ends of the cartridge plunger 120. The hooks are formed to provide a positive lock in groove 132 so that the cartridge plunger 120 may be withdrawn back into the cartridge bore after it has been moved distally to expel the preloaded material 102.

FIG. 8C is a cross-section taken through the prongs 124, at the location shown in FIG. 8A. In FIG. 8C, two legs 124 are located on opposite sides of the central opening 126, however the cartridge plunger may be fabricated with three or more legs if desired. In use, the legs 124 of the preloaded cartridge slip easily over the carrier plunger 130 until the legs 124 snap into groove 132. After the cartridge is used, it may be easily removed by tipping the cartridge slightly sideways so that the distal portion 131 of the plunger levers the legs 124 apart slightly to disengage the hooks 128 from the groove 132.

Figure 9:
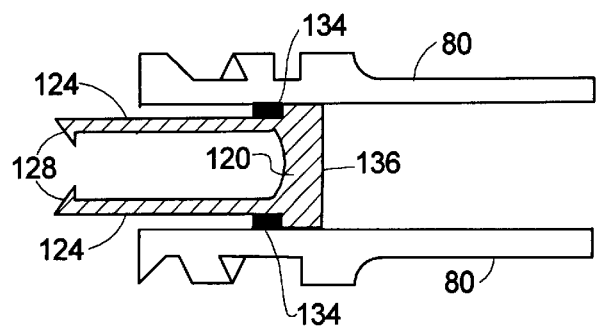
FIG. 9 shows a modification of the cartridge of FIG. 8A.

FIG. 9 shows a further modification of the cartridge of FIG. 8. In FIG. 9, a cylindrical shoulder 134 is formed on the inside of the cartridge walls 80 a short distance back of the end of the plunger 120. The distal end 136 of the plunger is sized to fit snugly inside of the cartridge bore while the proximal portion is smaller in diameter, as shown in FIG. 9. The shoulder serves to provide a positive stop preventing the cartridge plunger 120 from coming out of the proximal end of the cartridge. The cartridge of FIG. 9 has legs 124 and catches 128 which cooperate with a modified carrier plunger such as that shown in FIG. 8B and described above.

Although the modifications shown in FIGS. 6 and 7 and in FIGS. 8 and 9 are shown with the cartridge embodiments shown in FIGS. 3 and 5 respectively, it should be appreciated that the modifications shown and explained with reference to FIGS. 6–9 may be used with any of the cartridge embodiments of the present invention.

There has been described a new and useful construction for a dental resin carrier with removable sleeves or cartridges. While the advantages of the present invention have been explained with reference to the exemplary embodiments described above, it should be appreciated that modifications to these embodiments will be made by those of ordinary skill in the art in applying the teachings of the invention to different situations and applications. In particular, it should be appreciated that the present invention can be used with lever-type carriers that differ in construction details from the particular configuration shown in FIG. 1, and thus the lever-actuated resin carrier of the present invention could be modified to include improvements to lever-actuated carriers such as those taught by the above-cited patents. For example, the present invention could be used with a lever-actuated carrier having a spring member that is unitary with the lever, as taught in the above-cited U.S. Pat. No. 4,355,976. Accordingly, the present invention should not be limited by the embodiments described above, but rather the scope of the invention should be interpreted only in accordance with the following claims.

What is claimed is:

1. In a dental instrument for dispensing a dental material of the type having: a handle; a plunger in the form of an elongate bent rod connected at its proximal end to the handle, having a straight section at its distal end, and including a hook-shaped section between said proximal end and straight section; a lever having an elongate opening in the distal portion and having a finger-actuatable means at its proximal portion, the proximal and distal portions being connected to form an angle therebetween to provide a fulcrum; and means for mounting the lever to the handle and plunger assembly so that the plunger straight section and hook extend through the elongate opening and so that movement of the finger actuation means rotates the lever about said fulcrum to move the opening distally and proximally along the straight section; the mounting means further including spring means for applying pressure to the lever so as to keep the opening in its distal-most position in the absence of force applied to the finger-actuation means, the improvement comprising:

a removable cartridge for carrying and dispensing the dental material including an elongate hollow cylindrical body adapted to be slidably mounted over the distal end of the plunger for containing the dental material; and means for attaching the cartridge to the opening in the lever so that it slides along the plunger distal end as the lever rotates, including:

a cylindrical receiving body, including:

a hollow guide section at its proximal end slidably mounted on the plunger straight section and an internally-threaded receiving section at its distal end; and means for attaching the receiving body to the lever opening and for preventing the receiving body from rotating; and an externally-threaded section at the proximal end of the cartridge body cooperative with the internally-threaded receiving section to retain the cartridge in position.

2. The dental instrument of claim 1 wherein the plunger, lever, receiving body and cartridge are arranged so that the distal end of the plunger extends into the cartridge a short distance in the absence of force applied to the finger-actuation means.

3. The dental instrument of claim 2 wherein the means for attaching includes a groove formed on the outside surface of the receiving section and cooperative with the edges of the lever opening to prevent the receiving body from rotating.

4. The dental instrument of claim 4 wherein the receiving body is made of a metal and the cartridge is made of a plastic material.

5. In a dental instrument for dispensing a dental material of the type having: a handle: a plunger in the form of an elongate bent rod connected at its proximal end to the handle, having a straight section at its distal end, and including a hook-shaped section between said proximal end and straight section; a lever having an elongate opening in the distal portion and having a finger-actuatable means at its proximal portion, the proximal and distal portions being connected to form an angle therebetween to provide a fulcrum; and means for mounting the lever to the handle and plunger assembly so that the plunger straight section and hook extend through the elongate opening and so that movement of the finger actuation means rotates the lever about said fulcrum to move the opening distally and proximally along the straight section; the mounting means further including spring means for applying pressure to the lever so as to keep the opening in its distal-most position in the absence of force applied to the finger-actuation means, the improvement comprising:

a removable cartridge for carrying and dispensing the dental material including an elongate hollow cylindrical body adapted to be slidably mounted over the distal end of the plunger for containing the dental material; and means for attaching the cartridge to the opening in the lever so that it slides along the plunger distal end as the lever rotates wherein the means for attaching includes an externally-threaded section at the proximal end of the cartridge body adapted to threadably engage the edges of the elongate opening in the lever.

6. The dental instrument of claim 5 further including a shoulder section located on the outside of the cartridge body distal to the end of the external threads by a distance slightly greater than the thickness of the edges of the lever opening.

7. The dental instrument of claim 6 wherein the cartridge is made of a plastic material.

8. The dental instrument of claim 6 wherein the cartridge is made of a metal material.

9. An article of manufacture, comprising:

a removable cartridge made of a plastic material and having an elongate, hollow, cylindrical body for carrying and dispensing a dental material;

the cartridge being adapted for use with a dental instrument for dispensing a dental material of the type having: a handle; a plunger in the form of an elongate bent rod connected at its proximal end to the handle, having a straight section at its distal end, and including a hook-shaped section between said proximal end and straight section; a lever having an elongate opening in the distal portion and having a finger-actuatable means at it proximal portion, the proximal and distal portions being connected to form an angle therebetween to provide a fulcrum; and means for mounting the lever to the handle and plunger assembly so that the plunger straight section and hook extend through the elongate opening and so that movement of the finger actuation means rotates the lever about said fulcrum to move the opening distally and proximally along the straight section; the mounting means further including spring means for applying pressure to the lever so as to keep the opening in its distal-most position in the absence of force applied to the finger-actuation means; and the lever opening including means for engaging a threaded cartridge;

the cartridge being adapted to be removably and slidably mounted over the distal end of the plunger and further including an externally-threaded section at the proximal end of the cartridge body adapted to threadably engage the engaging means in the lever; and a preloaded dental material located inside the hollow cartridge body.

10. The article of claim 9 further including:

a removable seal attached to the distal end of the cartridge; and a removable seal attached to the proximal end of the cartridge.

11. The cartridge of claim 9 wherein the cartridge externally-threaded section is adapted to threadably engage the edges of the distal end of the elongate opening in the lever.

12. The cartridge of claim 9 wherein the cartridge externally-threaded section is adapted to engage an internally-threaded receiving section mounted in the lever opening.

13. The cartridge of claim 9 further including a cylindrical cartridge plunger slidably mounted inside the hollow cartridge body proximal to the preloaded material so as to provide a protective seal to the proximal portion of the preloaded material.

14. The cartridge of claim 13 further including a removable seal attached to the distal end of the cartridge.

15. The cartridge of claim 13 further including means for releasably attaching the cartridge plunger to the instrument plunger to prevent the cartridge plunger from being expelled out of the distal end of the cartridge during use.

16. The cartridge of claim 13 further including one or more inwardly-extending projections at the distal end of the cartridge body located so as to prevent the cartridge plunger from being expelled from the distal end of the cartridge during use.

* * * * *

UNITED STATES PATENT AND TRADEMARK OFFICE
CERTIFICATE OF CORRECTION

PATENT NO.   : 6,159,009
DATED        : December 12, 2000
INVENTOR(S)  : Kenneth J. Berk, Fredrick M. Berk, Donald Berk, and Russell D. Jenkins Page 1 of 1

It is certified that error appears in the above-identified patent and that said Letters Patent is hereby corrected as shown below:

In column 3, line 4, change "unshaped" to --U-shaped--.

Signed and Sealed this

Tenth Day of July, 2001

*Attest:*

*Attesting Officer*

NICHOLAS P. GODICI
*Acting Director of the United States Patent and Trademark Office*